United States Patent [19]

Johnson et al.

[11] Patent Number: 4,943,734
[45] Date of Patent: Jul. 24, 1990

[54] INSPECTION APPARATUS AND METHOD FOR DETECTING FLAWS ON A DIFFRACTIVE SURFACE

[75] Inventors: Carl E. A. Johnson, Merrimack; Jay L. Ormsby, Salem, both of N.H.; Eric T. Chase, Andover; George S. Quackenbos, Neburyport; Sergey V. Broude, Acton; Abdu Bou dour, West Newton, all of Mass.

[73] Assignee: QC Optics, Inc., Burlington, Mass.

[21] Appl. No.: 373,914

[22] Filed: Jun. 30, 1989

[51] Int. Cl.$^5$ ............................................. G01N 21/88
[52] U.S. Cl. ..................................... 250/572; 356/431
[58] Field of Search .................. 250/562, 563, 572; 356/430, 431

[56] References Cited

U.S. PATENT DOCUMENTS 4,511,803 4/1985 Röss ..................................... 250/562
4,632,546 12/1986 Sick ..................................... 250/562
4,831,274 5/1989 Kohno ................................ 250/572
4,866,288 9/1989 Weber ................................ 356/431

Primary Examiner—David C. Nelms
Assistant Examiner—Sherrie Hsia
Attorney, Agent, or Firm—Joseph S. Iandiorio

[57] ABSTRACT

An optical inspection system and method for detecting flaws on a diffractive surface such as a reticle or wafer, includes illuminating a surface to be inspected to generate a first scattered energy angular distribution in response to a flaw on the surface and a second scattered energy angular distribution in response to an unflawed surface; the first and second energy distributions are sensed and the minimum energy detection energy level is established; determining whether the minimum detected energy level is in a first or second predetermined energy range and indicating that no flaw is present when the minimum detected energy level is in the first range and a flaw is present when the minimum detected energy level is in the second range.

16 Claims, 5 Drawing Sheets

INSPECTION APPARATUS AND METHOD FOR DETECTING FLAWS ON A DIFFRACTIVE SURFACE

FIELD OF INVENTION

This invention relates to an optical inspection system for uniquely detecting the presence of particles on a surface with pattern features, and more particularly, to such a system which differentiates between light scattered by a pattern on the surface and light scattered by a particle.

BACKGROUND OF INVENTION

Several attempts have been made to develop systems for detecting particles on a surface with diffractive pattern features. For example, the system disclosed in U.S. Pat. No. 4,402,607 by McVay et al., assigned to the same assignee as the instant application, is adapted to detect dust or other minute particles on an optically polished surface such as a reticle with a standard, highly ordered, pattern on the surface. Although radiation scattering from the pattern accompanies radiation scattered by a particle or flaw, the effect of scattering caused by the pattern is minimized by utilizing a scanning light beam which approaches the surface under inspection at an acute angle. By analyzing only the backscattered component of the light scattered by the surface being inspected, it is believed that only light scattered by a flaw is detected, recorded and analyzed.

Many applications of such equipment require inspection of reticles with regular patterns oriented at 0°, 45°, 90°, or 135° from the plane of incidence of the light beam on the surface under inspection. Accordingly, U.S. Pat. No. 4,772,127, Chase et al., assigned to the same assignee as the instant application, discloses that by properly orienting the radiation detector in relation to the surface, for example at 60° or 120° from the direction of incidence of the light beam, backscattered radiation from 45° and 135° patterns is not detected, and therefore only radiation scattered from patterns at 90° to the direction of incidence of the beam need to be masked. Since a 90° pattern scatters radiation 180° back from the direction of the light source, the system places an array of shutters between an optical receiver and the surface under inspection. By closing the appropriate shutter located over the current position of the scanning beam, the scattered light which is due to the 90° pattern is blocked from reaching the receiver, and only side-scattered radiation from a surface flaw of a foreign particle reaches the radiation detector.

Many problems exist in this approach, however. This system and approach presumes that only regular patterns will exist on the surface. This approach further presumes that only 90° patterns will need to be blocked out. If other angular pattern geometries or combinations of angular patterns exist, the user of the system must have a prior knowledge of these patterns and must be able to predict at what angles the scattering of radiation will occur. In either case, the system must be programmed to generate the necessary signals to synchronize the shutter with the scanning of the beam to block out unwanted reflected pattern radiation diffracted by the pattern. In addition, the shutters which are utilized are generally piezoelectric devices which require a high voltage and are relatively slow to operate.

SUMMARY OF INVENTION: I

It is therefore an object of this invention to provide an improved optical inspection apparatus and method for detecting the presence of flaws on a diffractive surface.

It is a further object of this invention to provide such an apparatus and method which admit of much greater tolerance of position of the scanning beam and detector relative to the surface being inspected.

It is a further object of this invention to provide such an apparatus and method which do not require shutters and their attendant control and drive circuitry.

It is a further object of this invention to provide such an apparatus and method which can detect flaws even on patterned optically polished surfaces.

It is a further object of this invention to provide such an apparatus and method which are fast, efficient and economical.

This invention results from the realization that flaws produce a broad and continuous angular distribution of scattering of a substantial magnitude while regular surface patterns produce a plurality of relatively narrow angular scattering peaks separated by zero or very low energy angular intervals and that, therefore, the detection of a zero or very low energy scattering at some angle of scattering at an instant level during a scan is an indication that there is no flaw present at the point where the beam strikes the surface. The invention also results from the realization that if the optical viewing head includes a plurality of elements arranged in groups or segments, each group or segment of elements is sized to coincide with the area of scattering from the smallest flaw to be detected, and correspondingly located elements in each segment are connected to the same photoelectric sensor, then even the smallest flaw will produce sufficient scattered energy to indicate a flaw, and a zero or null reading from at least any one of a plurality of photoelectric sensors will indicate no flaw present.

This invention features an optical inspection system for detecting flaws on a diffractive surface. There are means for illuminating a surface to be inspected in order to generate a first scattered energy angular distribution in response to a flaw on the surface, and a second scattered energy angular distribution in response to an unflawed surface. There are means for sensing the first and second energy distributions and means responsive to the means for sensing for establishing the minimum detected energy level. There are also means for determining whether the minimum detected energy level is in a first or second predetermined energy range. Means responsive to the means for determining indicate that no flaw is present when the minimum detected energy level is in the first range, and indicates that a flaw is present when the minimum detected energy level is in the second range.

In a preferred embodiment the first range includes a noise level and the second range is above the noise level; or, the first range is generally zero and the second range is above zero; or, the first range extends above the noise level. The means for illuminating may include means for producing a narrow beam of radiation which may be a laser, and the means for illuminating may further include means for scanning the narrow beam across the optically polished surface. The means for sensing may include a plurality of photocells for monitoring a scan line illuminated by the means for illuminating. The means for sensing may also include an optical head including a set of segments, each segment including a plurality of elements, the segments and elements being aligned in the direction of the scan line. The optical head may also include a number of sets of segments adjacent to one another and aligned with the direction of the scan line. The number of photocells corresponds to the number of elements in a segment. Each photocell is connected to one element in each segment. The element in each segment to which a particular photocell is connected is in the same position in each segment. The means for establishing the minimum detected energy levels may include a minimum level detector responsive to the photocells. The means for determining may include a reference level defining the first and second ranges and comparator means, responsive to the means for establishing the minimum detected energy level and the reference level.

The invention may also feature an optical inspection method for detecting flaws on a diffractive surface by illuminating a surface to be detected by generating a first scattered energy distribution in response to a flaw on the surface, and a second scattered energy distribution in response to an unflawed surface. The first and second energy distributions are sensed and the minimum detected energy level is established. A determination is made as to whether the minimum detected energy level is in a first or second predetermined energy range. An indication is then provided that no flaw is present when the minimum detected energy level is in the first range and an indication that a flaw is present is made when the minimum detected energy level is in the second range.

DISCLOSURE OF PREFERRED EMBODIMENT

Other objects, features and advantages will occur from the following description of a preferred embodiment and the accompanying drawings, in which.

Figure 1:
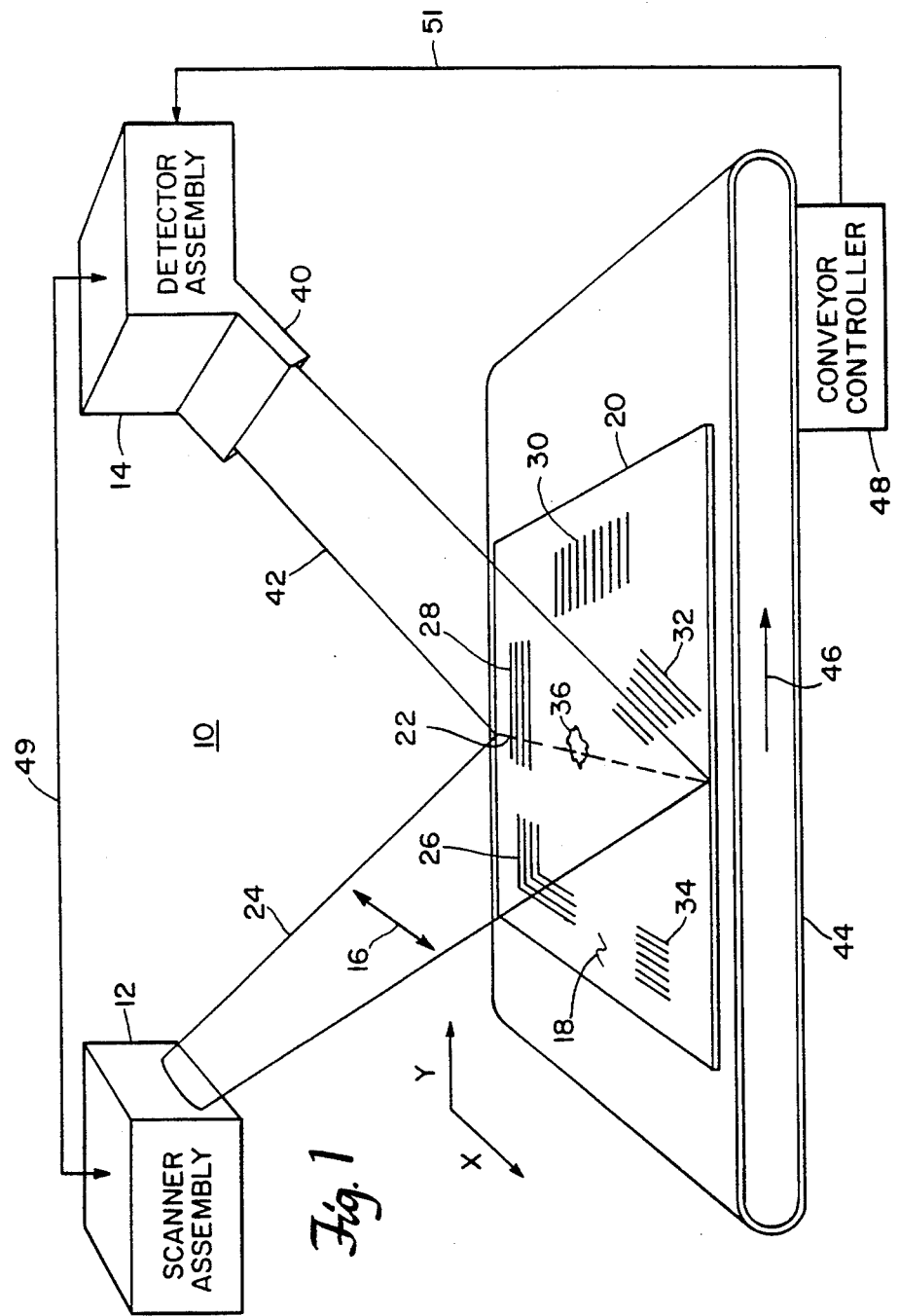
FIG. 1 is a schematic block diagram of an optical inspection system including a scanner assembly and detector assembly for inspecting an optically polished regular patterned surface, according to this invention.

There is shown in FIG. 1 an optical inspection system 10 according to this invention including a scanner assembly 12 and a detector assembly 14. Scanner assembly 12 includes a beam source such as a laser which provides a beam that is scanned in the direction of arrow 16 across the surface 18 of plate 20 to produce a scan line 22. Plate 20 may be a reticle used in the manufacture of electronic circuits, a semiconductor wafer, or other such plate having a patterned surface. The extent of scanning is indicated by the planar area 24. Surface 18 may include a plurality of regular patterns 26, 28, 30, 32, and 34, and an occasional flaw 36. As the beam is scanned in the direction of arrow 16 forming scan line 22, the optical head portion 40 of detector assembly 14 receives the radiation scattered from surface 18 in the field of view represented by plane 42. Each time scan line 22 is completed in the X direction, the conveyor 44 advances the surface under inspection in the Y direction as indicated by arrow 46 in preparation for the next X scan under direction of the conveyor controller 48. Detector assembly 14 receives inputs from both the conveyor controller 48 and scanner assembly 12 over lines 51 and 49, respectively, so that if a flaw such as flaw 36 is detected, the electronic portion of detector assembly 14 can quickly determine the X and the Y coordinates of the flaw location.

Figure 2:
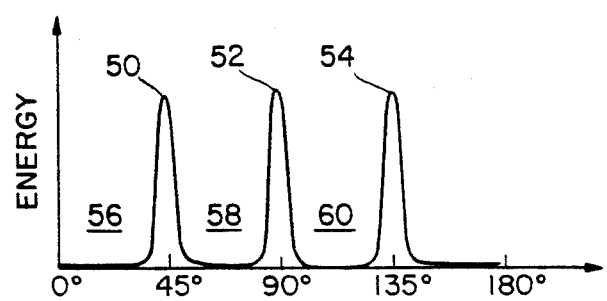
FIG. 2 illustrates the energy distribution from a regular surface pattern.

The angular energy distribution in plane 42 sensed by detector 14 in response to the illumination of a regular surface pattern is shown in FIG. 2 as consisting of peaks 50, 52, 54, of substantial energy levels, well defined, and separated by intervals 56, 58 and 60 which are extremely low, at the noise level and below, in some cases as low as zero.

Figure 3:
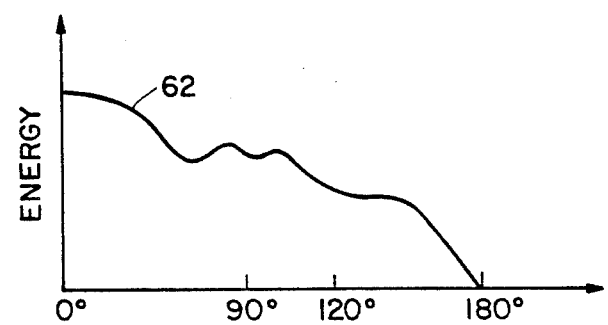
FIG. 3 illustrates the energy distribution from a flaw.

In contrast, a flaw such as flaw 36 produces an energy distribution in plane 42 as indicated by curve 62, FIG. 3, which is at a continuously high energy level with no zero or even low intervals. Thus when evaluating the intensity distribution from a particular location within a scan line, if there appears a zero or an extremely low level at any point, then it is clear that at this location there can be no flaw present: a flaw would provide a background level such as 62, FIG. 3, which would prevent any low level interval such as 56, 58 or 60, from appearing as the signal.

Figure 4:
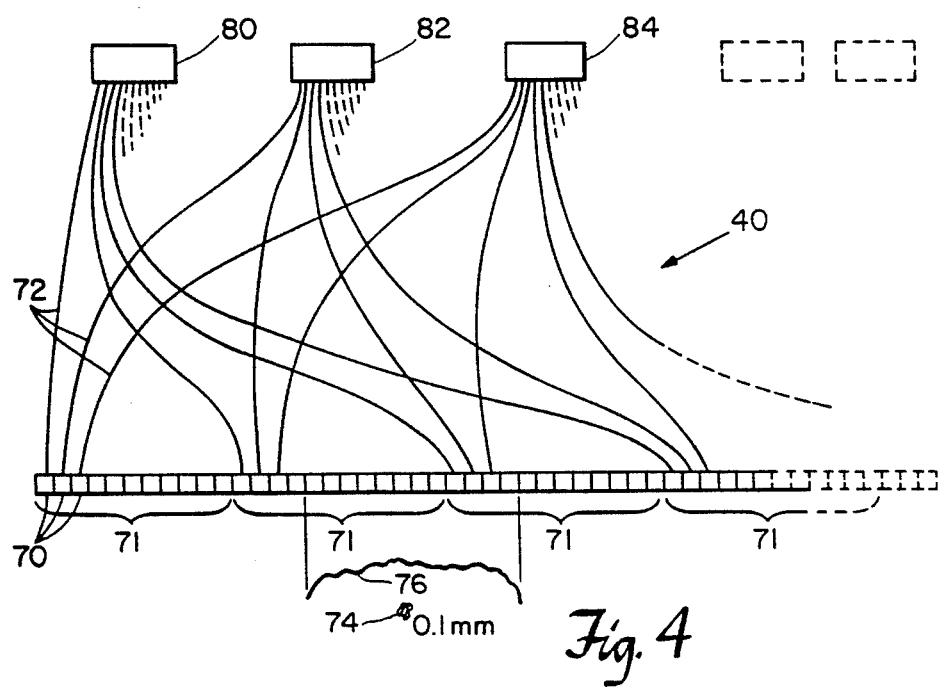
FIG. 4 is a schematic diagram of a portion of an optical head of the detector assembly of FIG. 1.

Optical head 40 is shown in greater detail in FIG. 4, where it includes a plurality of individual elements 70 which are actually the ends of optical fiber bundles indicated schematically in only single lines 72. In FIG. 4 there are actually one hundred twenty elements 70 arranged in ten groups or segments 71 of twelve elements each. Each element is approximately 2 mm long by 0.5 mm wide so that twelve of them make up a length of 24 mm. This size is chosen because the minimum expected flaw is approximately 0.5 mm as indicated at 74 and that size flaw can produce an energy distribution from light scattering covering a region as great as 24 mm. Thus the scattering from a flaw will cover as much as twelve elements, but the twelve elements need not be in the same group. For example, the energy distribution curve 76 (presented here as a polar diagram) characteristic of flaw 74 extends from the fourth element in the second group to the fourth element in the third group or segment. The elements in each group are connected to twelve photodetectors, only three of which, 80, 82, 84, are shown. The first element of each group or segment are all connected to photodetector 80. The second element in each group or segment is connected to the second photodetector 82. The third element in each group or segment is connected to the third photodetector 84, and so on. Thus a flaw appearing at any place along the surface provides a high level as indicated by curve 76 to a set of at least twelve elements which may be in a single group or segment or overlapping in a plurality of groups or segments. Since one of those elements is connected to each of the twelve photodetectors 80 82, 84, . . . , each of the photodetectors has an output which is substantially higher than any interval such as 56, 58 and 60, FIG. 2. Therefore, there must be a flaw present. If any one of the photodetectors 80, 82, 84, . . . , indicates a zero level or a very low level below some threshold, the electronics interprets this as an absence of flaws. All this is accomplished without any moving parts—shutters, selective mechanical devices, or the requirement for high voltage or synchronization.

Figure 5:
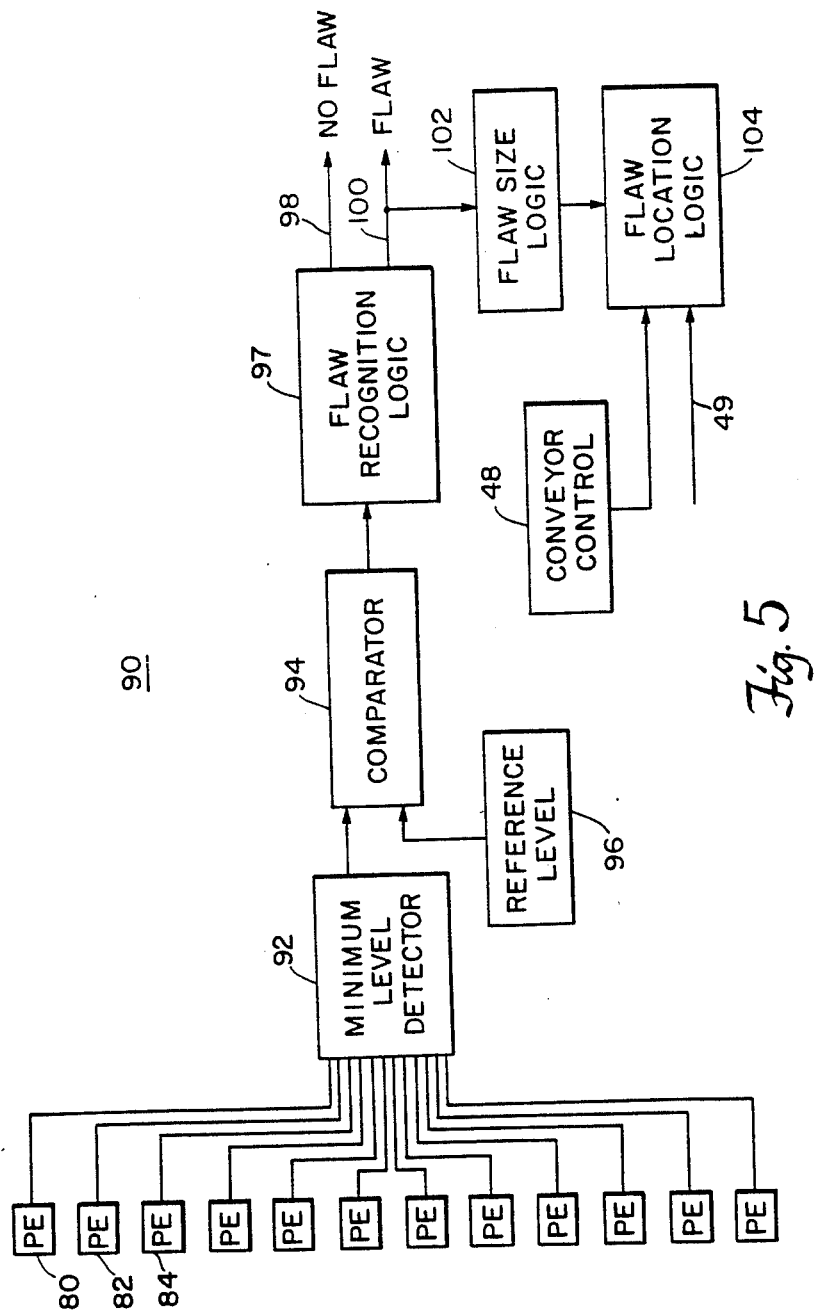
FIG. 5 is a schematic block diagram of the electronic detector portion of the detector assembly of FIG. 1.

The electronic portion of detector assembly 14 is depicted by electronic detection circuit 90, FIG. 5. There, each of the twelve photoelectric detectors 80, 82, 84, . . . , is connected to minimum level detector 92 which determines the lowest signal among those detected with photoelectric detectors 80, 82, 84, . . . This level is submitted to comparator 94, which compares it to a reference level from reference level circuit 96. This level may be at zero, somewhat above zero, at the noise level, or even above the noise level, depending upon the sensitivity and the conditions. If comparator 94 indicates that the lowest of twelve detected levels is below the reference level, then flaw recognition logic 97 puts out a no flaw signal on line 98. If, however, comparator 94 indicates that the lowest of twelve detected levels is above the reference level, then the flaw recognition logic 97 puts out a flaw signal on line 100. This signal can be further processed by flaw size logic 102 to indicate the size of the flaw since the level of the signal is representative of the size of the flaw. The flaw may also be located using flaw locator logic 104, which receives as input the Y position of plate 20 from conveyor control 48 on line 51, and the scanner position on line 49 from scanner assembly 12.

Figure 6:
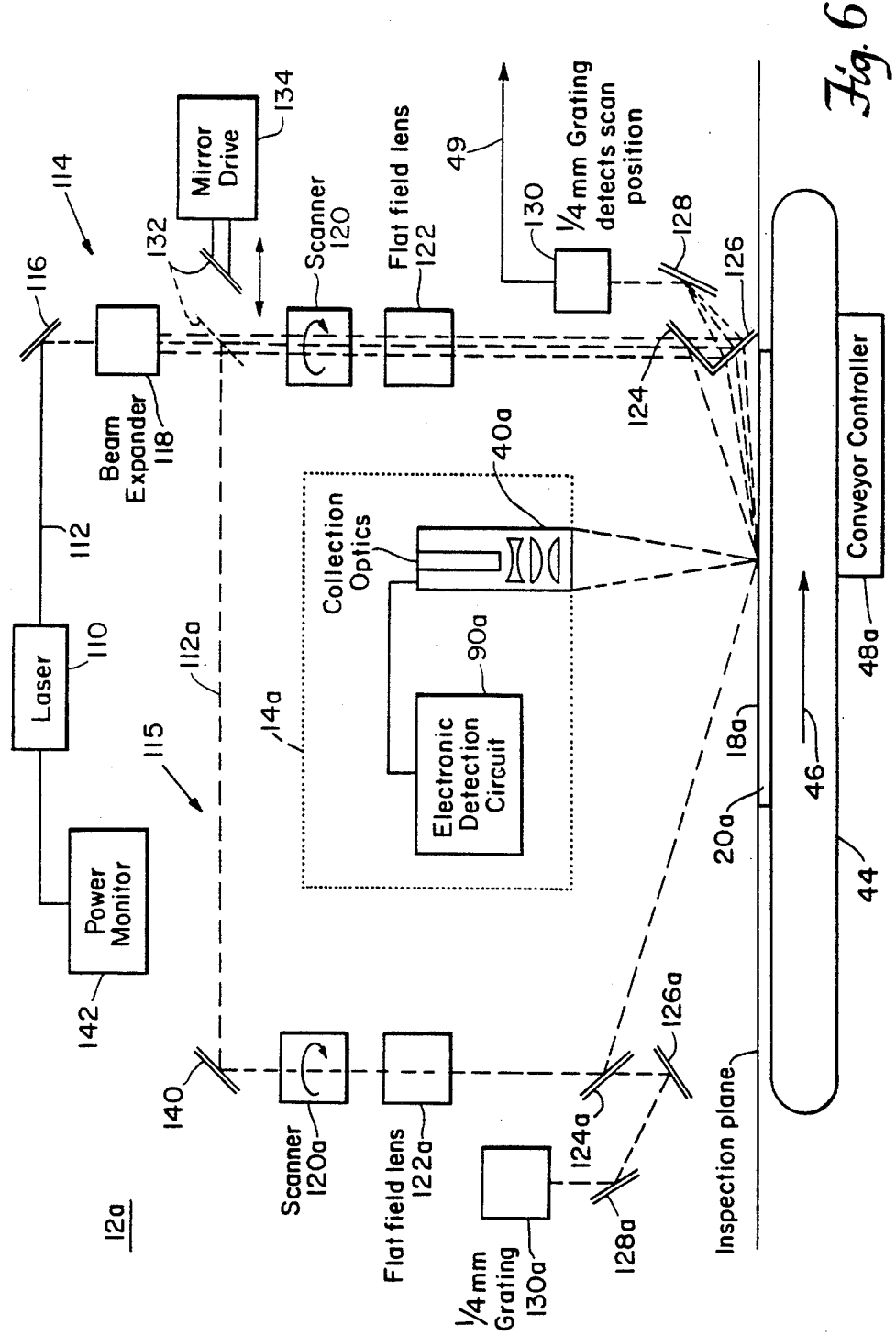
FIG. 6 is a more detailed schematic diagram of a scanner assembly usable in this invention.

In one construction, scanner assembly 12a, FIG. 6, may include a helium cadmium laser 110 which provides a narrow beam 112 in a first channel 114 and includes directional mirror 116, beam expander 118, scanner or beam sweeper 120, and a flat field scanning lens 122. From lens 122 the beam is delivered by mirror/beamsplitter 124 directly to the surface 18a of plate 20a, which is carried by conveyor 44. Mirrors 126 and 128 may be used to reflect a portion of the beam 112 to scan position detector 130 which provides the position information on line 49. A second beam 112a can be generated in second channel 115 by shifting mirror 132 into the dotted position by means of mirror drive 134. Beam 112a is redirected by mirror 140 to scanner 120a, flat-field scanning lens 122a, and thence from mirror/beamsplitter 124a to the surface 18a of plate 20a. Another pair of mirrors 126a and 128a may be provided to redirect a portion of beam 112a to another scan position detector 130a. Power monitor 142 is provided to control the laser output power. Light scattered from surface 18a is collected by optical head 40a and delivered to electronic detection circuit 90a in detector assembly 14a.

Figure 7:
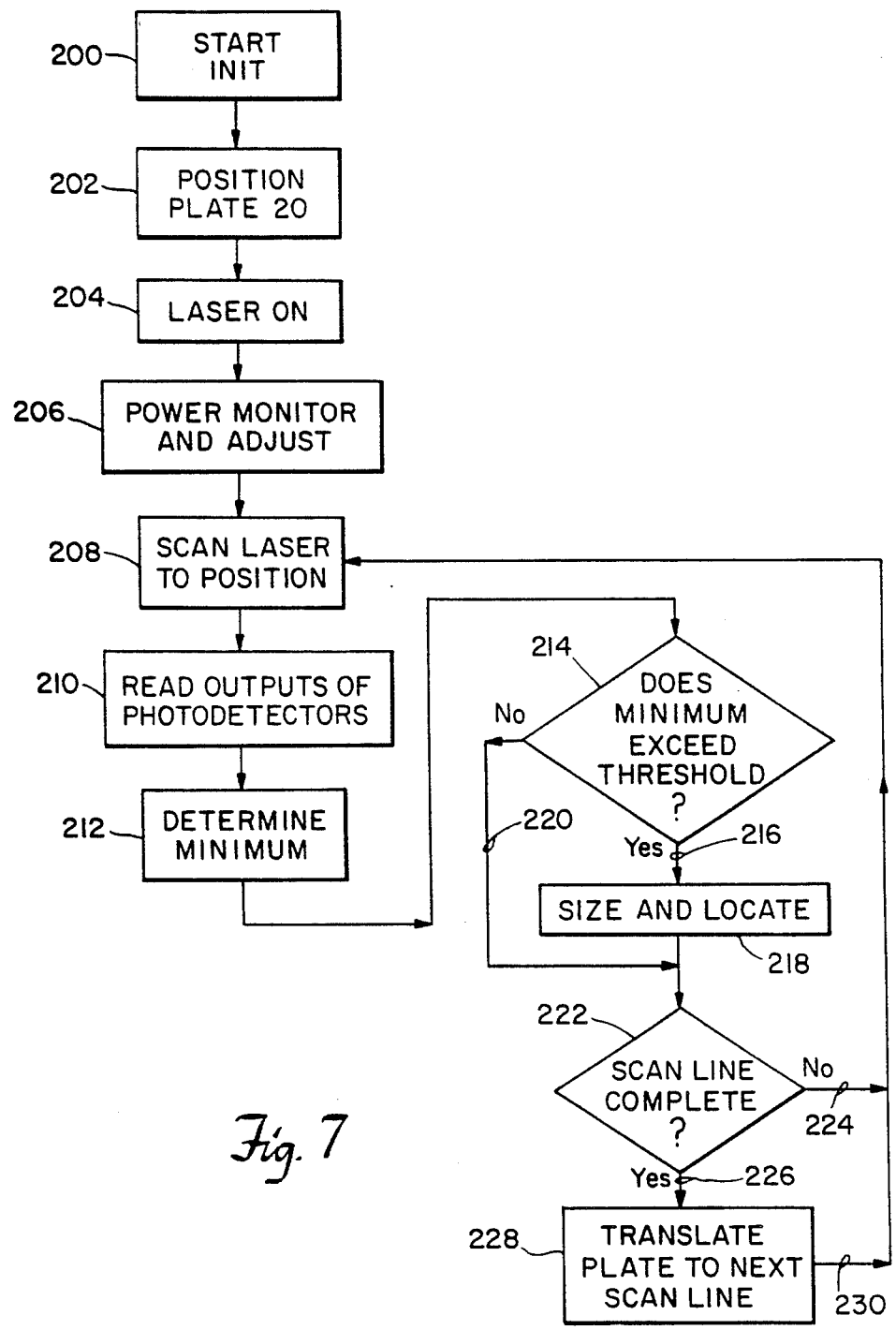
FIG. 7 is a flow chart depicting the method of this invention.

In carrying out the method of this invention, the system is initialized, step 200, FIG. 7, and plate 20 is positioned on conveyor 44, step 202. The laser 110 or other source is turned on, step 204, and the power monitor is used to adjust the beam to a constant selected level, step 206. The laser beam is then scanned across the surface, step 208 and the energy distribution output is read, step 210, by the photodetectors in optical head 40 of detector assembly 14. The output of the photodetectors is continuously processed by the electronic detection circuits 90 to determine the minimum detected level, step 212. If the minimum detected level exceeds a predetermined threshold, step 214, then a flaw is indicated at 216 and the size and location of that flaw can be provided, step 218. If the minimum detected level does not exceed the threshold, then the system moves along path 220 and avoids the size and location step 218. At this point, whether the threshold has been exceeded or not, inquiry is made as to whether the scan line is complete, step 222. If it is not, the system returns along loop 224 to step 208 where the laser scan is positioned. If the scan line is complete, then the conveyor is moved to translate the plate to the next scan line position, step 228, and the system returns over loop 230 to step 208 where the scan laser is positioned once again.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. An optical inspection system for detecting flaws on a diffractive surface, comprising:
   means for illuminating a surface to be inspected to generate a first scattered energy angular distribution in response to a flaw on the surface, or a second scattered energy angular distribution in response to an unflawed surface;
   means for sensing said first and second energy distributions;
   means, responsive to the means for sensing, for establishing the minimum detected energy level within said angular distribution;
   means, for detecting whether said minimum detected energy level is in a first predetermined energy range or a second predetermined energy range; and
   means, responsive to said means for determining, for indicating that no flaw is present when said minimum energy detection level is in said first range and a flaw is present when said minimum detected energy level is in said second range.

2. The system of claim 1 in which said first range includes the noise level and said second range is above the noise level.

3. The system of claim 1 in which said first range is generally zero and said second range is above zero.

4. The system of claim 1 in which said first range extends above the noise level.

5. The system of claim 1 in which said means for illuminating includes means for producing a narrow beam of radiation.

6. The system of claim 5 in which said means for producing includes a laser.

7. The system of claim 5 in which said means for illuminating includes means for scanning said narrow beam across said diffractive surface.

8. The system of claim 1 in which said means for sensing includes a plurality of photocells for monitoring a scan line illuminated by said means for illuminating.

9. The system of claim 8 in which said means for sensing includes an optical head including a set of segments, each segment including a plurality of elements, said segments and elements being aligned with the direction of said scan line.

10. The system of claim 9 in which the number of photocells corresponds to the number of elements in a segment.

11. The system of claim 10 in which each photocell is connected to one element in each segment.

12. The system of claim 11 in which the element in each segment to which a particular photocell is connected is in the same position in each segment.

13. The system of claim 8 in which said means for establishing the minimum detected energy level includes a minimum level detector responsive to said photocells.

14. The system of claim 1 in which said means for determining includes a reference level defining said first and second ranges and comparator means responsive to said means for establishing the minimum detected energy level and said reference level.

15. The system of claim 9 in which said optical head includes a number of sets of segments adjacent to one another and aligned with the direction of said scan line.

16. An optical inspection method for detecting flaws on a diffractive surface, comprising:

illuminating a surface to be inspected to generate a first scattered energy angular distribution in response to a flaw on the surface and a second scattered energy angular distribution in response to an unflawed surface;

sensing the first and second energy distributions;

establishing the minimum detected energy level;

determining whether the minimum detected energy level is in a first or second predetermined energy range; and indicating that no flaw is present when the minimum detection energy level is in the first range and that a flaw is present when the minimum detection energy level is in the second range.

* * * * *